(12) United States Patent
Rud

(10) Patent No.: US 9,857,228 B2
(45) Date of Patent: Jan. 2, 2018

(54) PROCESS CONDUIT ANOMALY DETECTION USING THERMAL IMAGING

(71) Applicant: Rosemount Inc., Chanhassen, MN (US)

(72) Inventor: Jason Harold Rud, Mayer, MN (US)

(73) Assignee: Rosemount Inc., Chanhassen, MN (US)

( * ) Notice: Subject to any disclaimer, the term of this patent is extended or adjusted under 35 U.S.C. 154(b) by 0 days.

(21) Appl. No.: 14/224,814

(22) Filed: Mar. 25, 2014

(65) Prior Publication Data

US 2015/0276491 A1 Oct. 1, 2015

(51) Int. Cl.
*G01J 5/10* (2006.01)
*G01N 25/72* (2006.01)
*G01J 5/00* (2006.01)

(52) U.S. Cl.
CPC ............... *G01J 5/10* (2013.01); *G01N 25/72* (2013.01); *G01J 2005/0077* (2013.01)

(58) Field of Classification Search
CPC ............................... G01N 25/72; G01N 25/00
See application file for complete search history.

(56) References Cited

U.S. PATENT DOCUMENTS

| | | | |
|---|---|---|---|
| 4,736,250 A | 4/1988 | Blazo | |
| 4,900,161 A | 2/1990 | Wolf et al. | |
| 5,056,046 A | 10/1991 | Mutchler | |
| 5,109,277 A | 4/1992 | James | |
| 5,144,430 A | 9/1992 | Boelart | |
| 5,292,195 A | 3/1994 | Crisman, Jr. | |
| 5,654,977 A * | 8/1997 | Morris | 374/4 |
| 6,000,844 A * | 12/1999 | Cramer | G01N 25/72 374/124 |

(Continued)

FOREIGN PATENT DOCUMENTS

| | | |
|---|---|---|
| AU | 2002256070 | 5/2006 |
| CN | 1214958 | 4/1999 |

(Continued)

OTHER PUBLICATIONS

Notification of Transmittal of the International Search Report and the Written Opinion of the International Searching Authority, PCT/US2015/011958, dated May 18, 2015.

(Continued)

*Primary Examiner* — Christine Sung
(74) *Attorney, Agent, or Firm* — Westerman, Champlin & Koehler, P.A.

(57) ABSTRACT

A diagnostic field device for detecting a condition of a process conduit includes an infrared detector comprising a plurality of pixels configured to receive infrared radiation from the process conduit and responsively provide a plurality of pixel outputs. A first pixel of the plurality of pixels is configured to receive infrared radiation from a first location on the process conduit. A second pixel of the plurality of pixels is configured to receive infrared radiation from a second location on the process conduit. A memory contains thermal profile information which relates an output from the first pixel to a first temperature at the first location and relates an output from the second pixel to a second temperature at the second location. A microprocessor identifies a process anomaly based upon outputs from the first and second pixels. Output circuitry provides a diagnostic output indicative of the identified process anomaly.

19 Claims, 6 Drawing Sheets

(56) References Cited

U.S. PATENT DOCUMENTS

| | | | |
|---|---|---|---|
| 6,059,453 | A | 5/2000 | Kempf et al. |
| 6,461,573 | B1 | 10/2002 | Yamamoto et al. |
| 6,518,744 | B1 | 2/2003 | Tallman |
| 6,573,331 | B1 | 6/2003 | Camberlin |
| 6,631,287 | B2 | 10/2003 | Newman et al. |
| 7,248,297 | B2 | 7/2007 | Catrysse et al. |
| 7,407,323 | B2 | 8/2008 | Hutcherson |
| 7,409,867 | B2 | 8/2008 | Toy et al. |
| 7,472,215 | B1 | 12/2008 | Mok et al. |
| 7,680,460 | B2 | 3/2010 | Nelson et al. |
| 7,809,379 | B2 | 10/2010 | Hedtke et al. |
| 8,108,790 | B2 | 1/2012 | Morrison, Jr. et al. |
| 8,191,005 | B2 | 5/2012 | Baier et al. |
| 8,410,946 | B2 | 4/2013 | Ansari et al. |
| 8,538,560 | B2 | 9/2013 | Brown et al. |
| 9,019,108 | B2 | 4/2015 | Chillar et al. |
| 9,201,414 | B2 | 12/2015 | Kantzes et al. |
| 9,201,419 | B2 | 12/2015 | Timsjo et al. |
| 2001/0042834 | A1* | 11/2001 | Kenway ............... 250/341.6 |
| 2003/0027949 | A1 | 2/2003 | Yamamoto et al. |
| 2004/0156549 | A1 | 8/2004 | Persiantsev |
| 2004/0218099 | A1 | 11/2004 | Washington |
| 2005/0008072 | A1 | 1/2005 | Angerer |
| 2005/0012817 | A1 | 1/2005 | Hampapur et al. |
| 2005/0164684 | A1 | 7/2005 | Chen et al. |
| 2005/0220331 | A1 | 10/2005 | Kychakoff et al. |
| 2006/0026971 | A1 | 2/2006 | Sharpe |
| 2006/0092153 | A1 | 5/2006 | Chu et al. |
| 2006/0148410 | A1 | 7/2006 | Nelson |
| 2006/0278827 | A1* | 12/2006 | Sierra ............... G01J 1/04 250/338.1 |
| 2007/0019077 | A1 | 1/2007 | Park |
| 2007/0052804 | A1 | 3/2007 | Money et al. |
| 2007/0073439 | A1 | 3/2007 | Habibi et al. |
| 2007/0125949 | A1 | 6/2007 | Murata et al. |
| 2008/0165195 | A1 | 7/2008 | Rosenberg |
| 2009/0078047 | A1 | 3/2009 | Dam |
| 2009/0249405 | A1 | 10/2009 | Karaoguz et al. |
| 2009/0285259 | A1 | 11/2009 | Allen et al. |
| 2010/0220180 | A1 | 9/2010 | Lee et al. |
| 2011/0230942 | A1 | 9/2011 | Herman et al. |
| 2012/0025081 | A1 | 2/2012 | Rapp et al. |
| 2012/0041582 | A1 | 2/2012 | Wallace |
| 2012/0161958 | A1 | 6/2012 | Turon et al. |
| 2013/0009472 | A1 | 1/2013 | Orth |
| 2013/0085688 | A1 | 4/2013 | Miller et al. |
| 2013/0099922 | A1 | 4/2013 | Lohbihler |
| 2013/0176418 | A1* | 7/2013 | Pandey ............... G01N 25/72 348/83 |
| 2013/0294478 | A1 | 11/2013 | Puroll et al. |
| 2014/0003465 | A1 | 1/2014 | Elke |
| 2014/0128118 | A1 | 5/2014 | Tomimatsu et al. |

FOREIGN PATENT DOCUMENTS

| | | |
|---|---|---|
| CN | 2694128 | 4/2005 |
| CN | 101046375 | 10/2007 |
| CN | 101647216 | 2/2010 |
| CN | 101681161 | 3/2010 |
| CN | 101685295 | 3/2010 |
| CN | 1012483618 | 5/2012 |
| CN | 102999022 | 3/2013 |
| EP | 2 130 187 | 4/2017 |
| JP | 62-179647 | 8/1987 |
| JP | 10-47312 | 2/1998 |
| JP | 11-23350 | 1/1999 |
| JP | 11-189603 | 7/1999 |
| JP | 11-218442 | 8/1999 |
| JP | 2000-310577 | 11/2000 |
| JP | 2001-221666 | 8/2001 |
| JP | 2005-134357 | 5/2005 |
| JP | 2011-185926 | 9/2011 |
| JP | 2011-209033 | 10/2011 |
| JP | 2012-037519 | 2/2012 |
| JP | 2012-58093 | 3/2012 |
| JP | 2013-533570 | 8/2013 |
| RU | 2 372 667 | 11/2009 |
| TW | I220364 | 8/2004 |
| WO | WO 2004/011935 | 2/2004 |
| WO | WO 2008/136752 | 11/2008 |
| WO | WO 2009/074708 | 6/2009 |
| WO | WO 2011/004020 | 1/2011 |
| WO | WO 2011/137264 | 11/2011 |
| WO | WO 2013/006307 | 1/2013 |
| WO | WO 2013-009715 | 1/2013 |

OTHER PUBLICATIONS

First Correct Notification for Chinese Patent Application No. 201420426405.7, dated Oct. 31, 2014, 4 pages.
Notification of Transmittal of the International Search Report and the Written Opinion of the International Searching Authority, PCT/US2014/051625, dated Oct. 23, 2014.
Notification of Transmittal of the International Search Report and the Written Opinion of the International Searching Authority, PCT/US2014/051432, dated Jan. 12, 2015.
Invitation to Pay Additional Fees, PCT/US2014/051628, dated Nov. 25, 2014.
Notification of Transmittal of the International Search Report and the Written Opinion of the International Searching Authority, PCT/US2014/069968, dated Mar. 19, 2015.
Office Action from Chinese Patent Application No. 201320868039.6, dated May 19, 2014.
DF-TV7-T, Multi-Spectrum 3IR Flame Detector, Groveley Detection Ltd., 2 pgs. no date.
DF-TV7-V, Combined UV/2IR Flame Detector, Groveley Detection Ltd., 2 pgs. no date.
FDS301, Visual Flame Detector FDS301, Groveley Detection Ltd., 2 pgs. no date.
Hardesty, Larry. (MIT News Office). MIT News "Researchers amplify variations in video, making the invisible visible," dated Jun. 22, 2012, 3 pgs. Found at http://web.mit.edu/newsoffice/2012/amplifying-invisible-video-0622.html.
Notification of Transmittal of the International Search Report and the Written Opinion of the International Searching Authority, PCT/US2014/051628, dated Apr. 13, 2015.
Office Action from U.S. Appl. No. 14/224,858, dated Jun. 12, 2015.
"Integrated Wireless Gas Detection Solution", www.gassecure.com, Jun. 2014, 2 pgs.
"GS01 Wireless Gas Detector", www.gassecure.com, Jun. 2014, 2 pgs.
Office Action from U.S. Appl. No. 14/224,858, dated Oct. 2, 2015.
Notification of Transmittal of the International Search Report and the Written Opinion of the International Searching Authority, PCT/US2015/040310, dated Nov. 11, 2015.
Office Action from U.S. Appl. No. 14/224,858, dated Feb. 5, 2016.
Communication from European Patent Application No. 15706956.8, dated Nov. 7, 2016.
Office Action from Chinese Application Serial No. 201310737591.6, dated Oct. 17, 2016.
Examination Report from Australian Application Serial No. 2014328666, dated Oct. 11, 2016.
Office Action from Chinese Application Serial No. 201410024656.7, dated Oct. 9, 2016.
Office Action from Canadian Application Serial No. 2,923,153, dated Jan. 16, 2017.
Office Action from Chinese Patent Application No. 201410061865.9 dated Oct. 28, 2016.
Office Action from U.S. Appl. No. 14/037,989, dated Jun. 3, 2016.
Office Action from European Application Serial No. 14761468.9, dated May 4, 2016.
Office Action from U.S. Appl. No. 14/038,090, dated Jun. 28, 2016.
Office Action from European Application Serial No. 14761467.1, dated May 4, 2016.
Office Action from Russian Application Serial No. 2016116020, dated May 31, 2016.

(56) References Cited

OTHER PUBLICATIONS

Office Action from European Application Serial No. 14783924.5, dated Jun. 3, 2016.
Examination Report from Australian Application Serial No. 2014328576, dated Jul. 21, 2016.
Office Action from Chinese Application Serial No. 201410366848.6, dated Feb. 25, 2017.
Office Action from Canadian Application Serial No. 2,923,156, dated Feb. 2, 2017.
Office Action from U.S. Appl. No. 14/037,989, dated Feb. 10, 2017.
Office Action from U.S. Appl. No. 14/499,719, dated Mar. 23, 2017.
Office Action (including Search Report) from Russian Application Serial No. 2016116020, dated Feb. 10, 2017.
Office Action from Australian Patent Application No. 2014328576, dated Feb. 24, 2017.
Office Action from Canadian Patent Application No. 2,923,159, dated Mar. 7, 2017.
Office Action from Japanese Patent Application No. 2016-516988, dated Mar. 24, 2017.
Office Action from Japanese Patent Application No. 2016-516933, dated Mar. 8, 2017.
Office Action from Canadian Patent Application No. 2,923,159 dated May 19, 2017.
Office Action from Canadian Patent Application No. 2,943,542, dated Jul. 31, 2017.
Office Action from Japanese Patent Application No. 2016-558794, dated Oct. 24, 2017.

\* cited by examiner

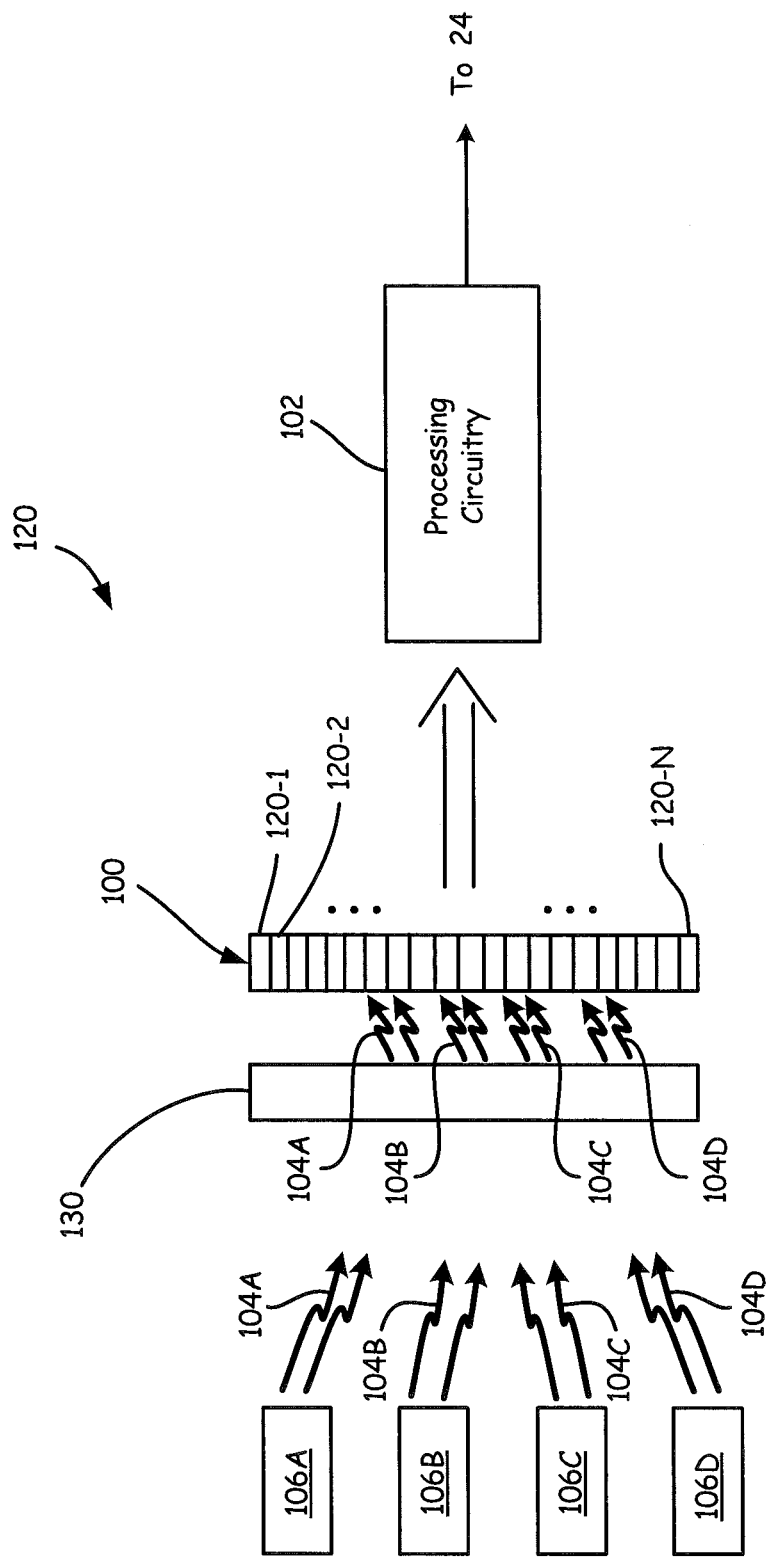

PROCESS CONDUIT ANOMALY DETECTION USING THERMAL IMAGING

BACKGROUND

The present invention relates to diagnostics of process control and monitoring systems of the type used in industrial processes. More specifically, the present invention relates to diagnostics which are based upon thermal imaging in industrial processes.

Industrial processes are used in the manufacture and movement of various process fluids. In such installations, piping is used to convey process fluid between various locations such as containers or other vessels. Piping, containers, as well as other types of vessels are examples of process conduits.

The various conduits used within an industrial process that carry process fluid may tend to degrade over time. One source of this degradation is due to exposure to excessive temperatures. Such excessive temperatures may result in a temperature gradient in the process which can be identified by an operator physically walking through an industrial plant carrying a handheld thermal imaging camera to obtain infrared surface temperature measurements. The operator must manually interpret the image information to determine if a temperature is outside of a specified range. This is time consuming and does not provide continuous monitoring of critical points within the process.

SUMMARY

A diagnostic field device for detecting a condition of a process conduit includes an infrared detector comprising a plurality of pixels configured to receive infrared radiation from the process conduit and responsively provide a plurality of pixel outputs. A first pixel of the plurality of pixels is configured to receive infrared radiation from a first location on the process conduit. A second pixel of the plurality of pixels is configured to receive infrared radiation from a second location on the process conduit. A memory contains thermal profile information which relates an output from the first pixel to a first temperature at the first location and relates an output from the second pixel to a second temperature at the second location. A microprocessor identifies a process anomaly based upon outputs from the first and second pixels. Output circuitry provides a diagnostic output indicative of the identified process anomaly.

BRIEF DESCRIPTION OF THE DRAWINGS

FIG. 6 is a simplified schematic diagram illustrating another example configuration of an infrared detector for use with the field device shown in FIG. 3.

DETAILED DESCRIPTION OF ILLUSTRATIVE EMBODIMENTS

As discuss in the Background section, infrared surface measurements of process conduits typically require an operator to physically walk through an industrial plant carrying a handheld thermal imaging device. The operator uses the thermal imaging device to manually collect data from critical points in the process. If these critical points are not monitored continuously, the temperature may exceed the limits of a material used to fabricate the conduit causing a failure leading to a premature shut down of the plant. As described below in more detail, a diagnostic device is provided which can identify anomalies in process conduits used in an industrial process based upon thermal imaging rather than employing temperature sensors which physically couple to components of the industrial process. This allows for automated monitoring of the process and does not require an operator to physically inspect the process. In one example embodiment, an infrared array is used to obtain a thermal image of the industrial process. Diagnostic circuitry performs diagnostics by monitoring the thermal image. Variations in the thermal image can be correlated to a failing conduit.

Figure 1:
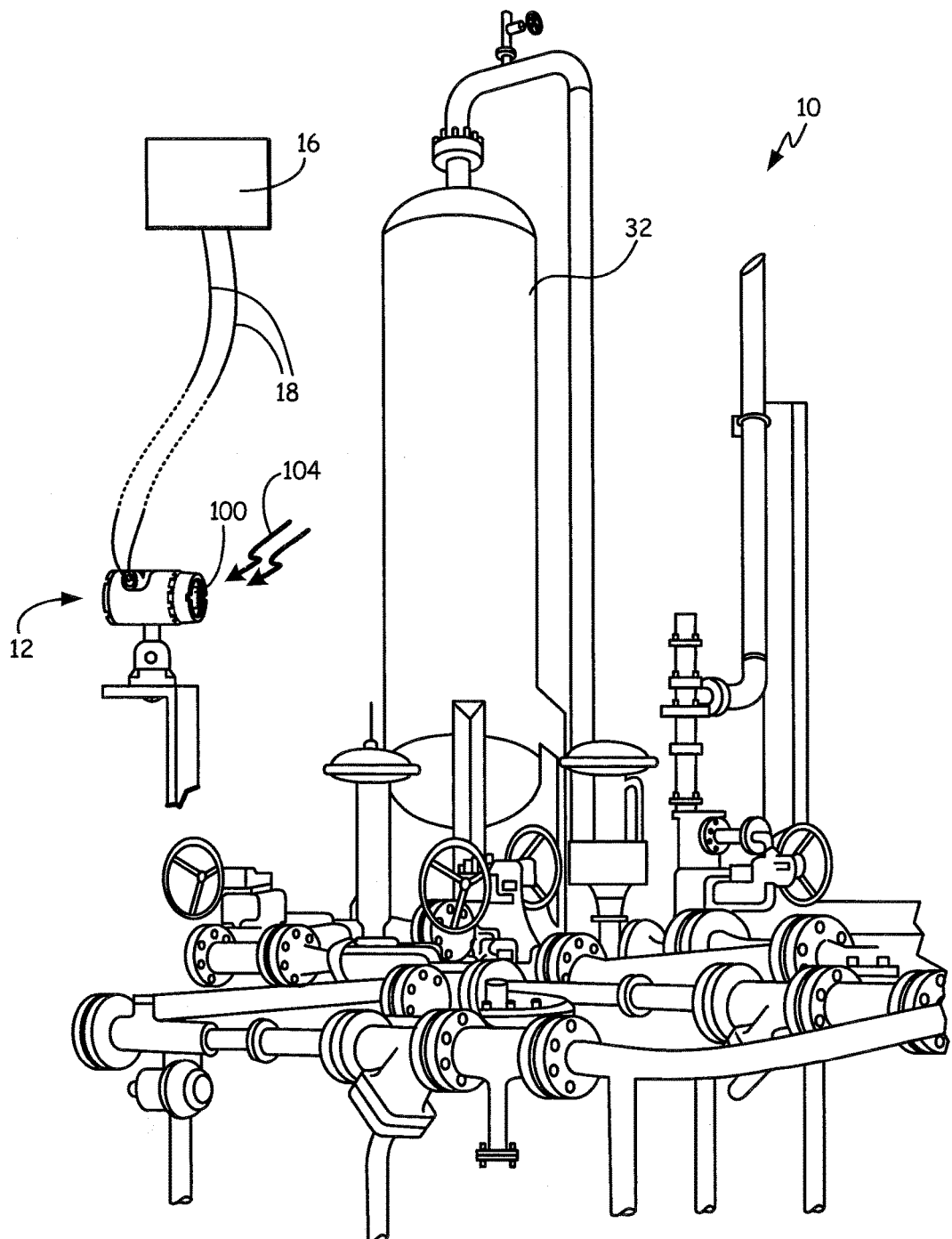
FIG. 1 is a simplified diagram showing an industrial process including a diagnostic field device.

FIG. 1 is a simplified diagram showing an industrial process 10 which includes a process diagnostic device 12 illustrating one embodiment of the invention. The device 12 can be any type of process device such as a stand-alone device, or process variable transmitter or controller. Device 12 couples to a another location such as process control room 16 over a two-wire process control loop 18. For example, loop 18 can comprise a 4-20 mA current loop that can also be used to power devices connected to the loop 18. Data can be carried on loop 18 in accordance with any appropriate protocol, for example, an analog current level which varies between 4 and 20 mA, the HART® communication protocol in which digital information is modulated upon a 4-20 mA current, a FieldBus or Profibus communication protocol, etc., including wireless communication techniques. One example of wireless communication technique is the Wireless HART® communication protocol in accordance with the IEC 62591. Standard Ethernet, fiberoptic connections, or other communication channels may also be used to implement loop 18. Control room 16 includes an optional display 19 discussed below in more detail.

As illustrated in FIG. 1, process device 12 includes an infrared detector 100 configured to receive infrared radiation 104, for example, from a conduit 32. Detector 100 can comprise an infrared thermal imaging camera. Conduit 32 is illustrated as a tank but may comprise any vessel which carries process fluid including process piping. Detector 100 may comprise an infrared sensor array. As described below in more detail, process device 12 is capable of detecting an anomaly in conduit 32 by monitoring infrared radiation 104.

Figure 2A:
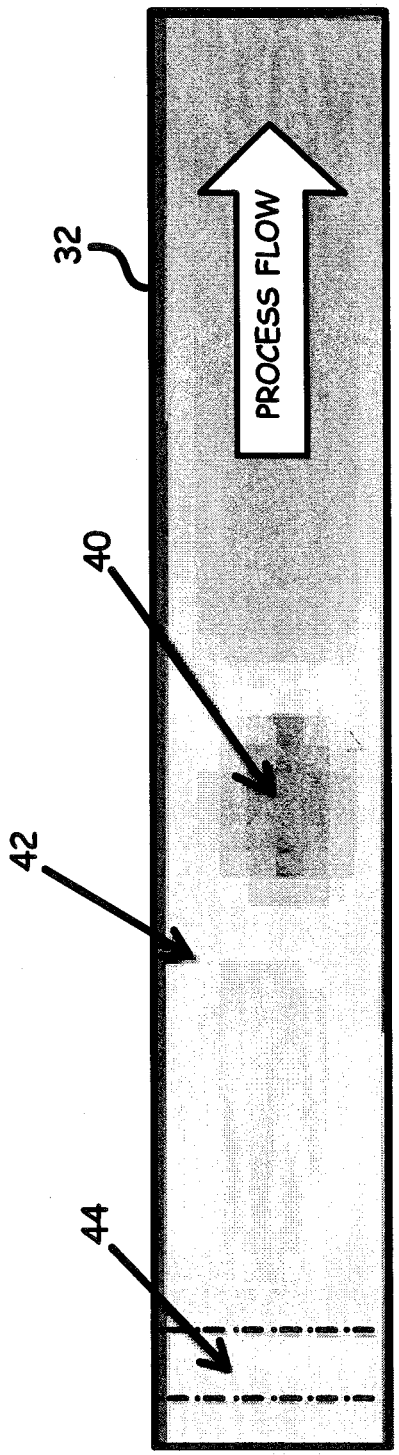
FIG. 2A is a side thermal image of a process conduit showing a process anomaly.

FIG. 2A is a side thermal image view of conduit 32 and illustrates a flow of process fluid. FIG. 2A also illustrates an anomaly 40 in the process conduit skin temperature 42 of conduit 32. Anomaly 40 is shown by the darker region in the figure which indicates a higher temperature than the surrounding areas. This region of localized heating may be due to any number of sources. For example, a hot object in the flow may positioned near wall of the conduit, the wall of the conduit may be thinning and has lost structural integrity, a heat source in the process may be affecting the conduit, etc. Although the anomaly 40 is illustrated as region of increased temperature, a process anomaly may also be detected by identifying localized cooling. The detected anomaly may indicated an impending failure or may indicate that a failure has already occurred. The anomaly 40 may be detected using the infrared detector 100 shown in FIG. 1 to monitor for hot or cold spots on conduit 32

Anomaly detection may be through any number of techniques. For example, normal temperature characteristics for conduit 32 due to process dynamics and inherent temperature variations can be learned. If thermal detector 100 is a thermal imaging device, a thermal image of the conduit 32 can be monitored at the pixel level to observe relative trends in the data to identify surface anomalies. An anomaly can be detected if a grouping of pixels have characteristics which are gradually changing over time in relation to other pixels in the thermal image. An alert can be provided to an operator along with information indicating where on the surface of the conduit 32 the anomaly 40 was observed.

Figure 2B:
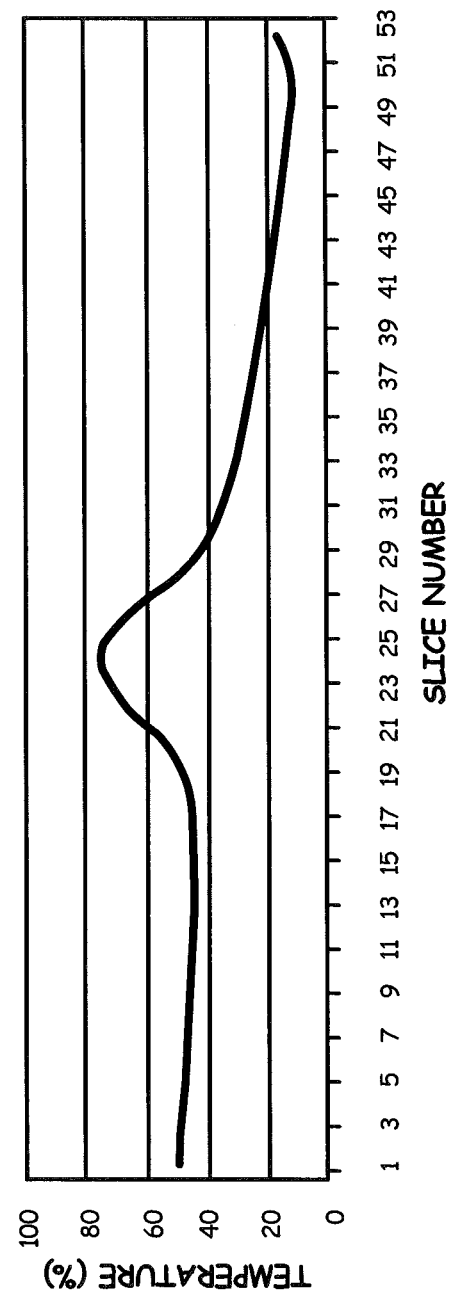
FIG. 2B is a temperature profile of a plurality of slices in the thermal image of FIG. 2A

The evaluation of the thermal image may be performed in a number of ways. For example, individual slices through the image can be monitored. A "slice" is one example of a portion of a thermal image which consists of more than one pixel. A slice is made up of pixels taken along cross section of the surface of conduit 32. FIG. 2A shows an example slice 44. An average temperature of each slice can be determined based on the pixels that make up the slice. FIG. 2B is a graph of individual slices in the thermal image taken along the length of conduit 32 versus temperature. In this example, the conduit 32 has a normal temperature profile which is generally linear. The anomaly 40 appears in FIG. 2B as non-linear region in this profile. The profile can be normalized to account for any variations which are part of normal process operation by using a learning cycle. Normal or expected temperature values can be subtracted from a measured temperature profile to account for such variations.

Figure 3:
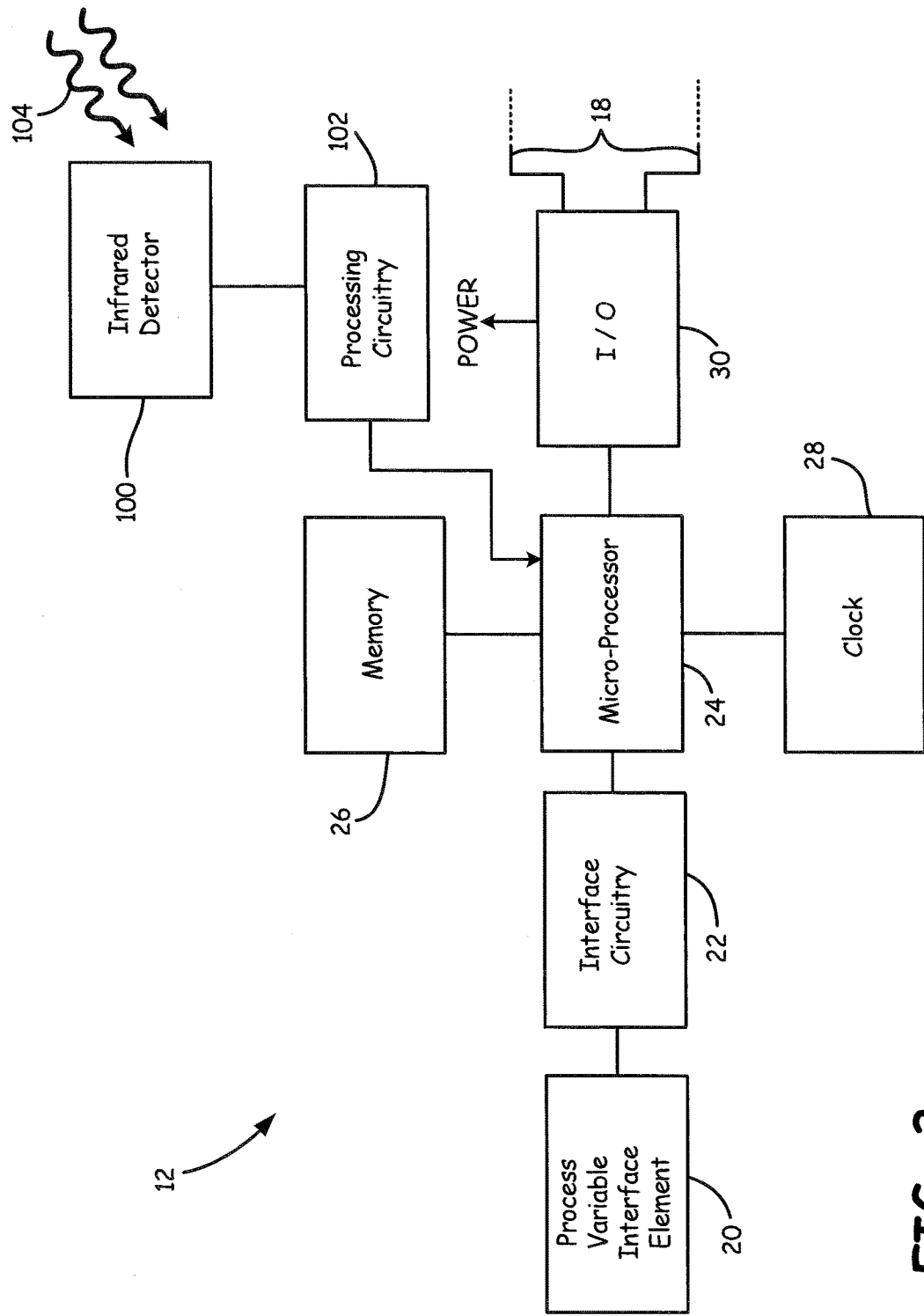
FIG. 3 is a simplified block diagram showing a process field device from FIG. 1.

FIG. 3 is a simplified block diagram of process device 12 according to an embodiment of the invention. Process device 12 can be configured as a standalone diagnostic device, or as a process variable transmitter or controller. Device 12 includes a microprocessor 24 which operates in accordance with instructions stored in memory 26 at a rate determined by clock 28. Communication circuitry (I/O) 30 is used for communicating on the process control loop 18. In some embodiments, I/O circuitry 30 also provides power to device 12.

FIG. 3 illustrates infrared detector 100 coupled to processing circuitry 102. Infrared detector 100 is configured to receive infrared radiation 104 and output a thermal image. Processing circuitry 102 provides optional pre-processing of a detected infrared image prior to providing the image to microprocessor 24. Note that FIG. 2 also illustrates an optional process variable interface element 20 and interface circuitry 22. The interface element 20 may be a process variable sensor or controller.

Detector 100 is arranged to receive infrared radiation 104 from process conduit 32 shown in FIG. 1. The detected infrared radiation forms a thermal or infrared image of the process conduit 32. The image is formed by a plurality of subsections or portions which correspond to different regions in the conduit 32. Infrared detector 100 is preferably directional and, as explained below in more detail, includes a plurality of individual infrared sensors ("pixels"). These sensors may be individual discrete elements or may be fabricated in a single device. The output from infrared detector 100 is provided to processing circuitry 102 illustrated in FIG. 3 which provides a processed output to the microprocessor 24. For example, processing circuitry 102 can include amplification circuitry, noise reduction circuitry, an analog to digital converter, comparison circuitry, etc. The output from processing circuitry 102 is provided to microprocessor 24 in a digital format.

Figure 4:
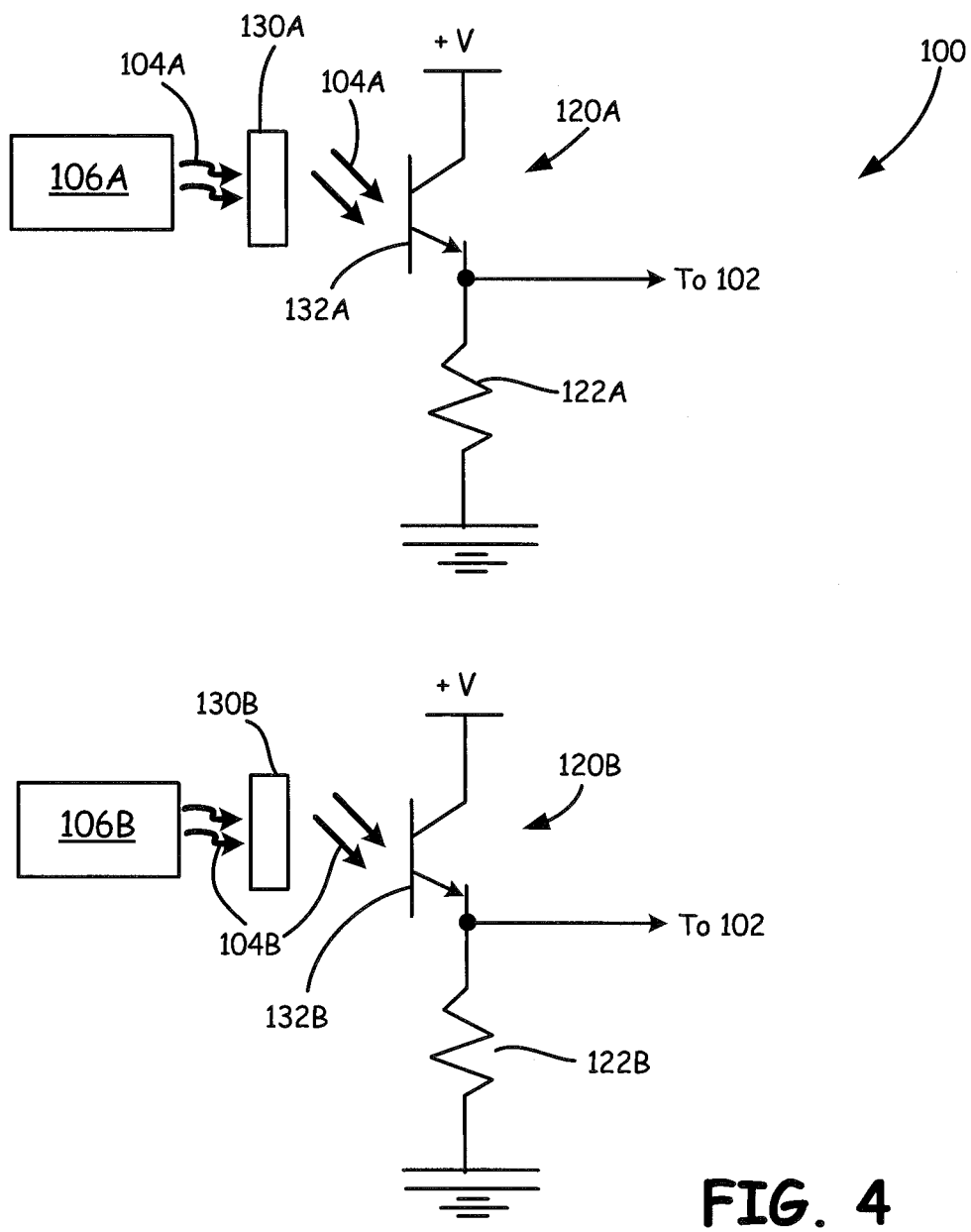
FIG. 4 is a simplified schematic diagram illustrating one example configuration of an infrared detector for use with the field device shown in FIG. 3.

In one example configuration, infrared detector 100 is formed of at least two individual infrared sensors 120A and 120B as illustrated in FIG. 4. In FIG. 4, the infrared detector 100 is configured to form an infrared (or thermal) image which comprises only two pixels formed by infrared sensors 120A and 120B. Each of these two pixels corresponds to a subsection or portion of the infrared image and sense infrared radiation from two locations 106A, 106B on process conduit 32. Locations 106A,B are examples of portions or "slices" of conduit 32. Each pixel can view a portion or "slice" of an image of conduit 32 as discussed above. FIG. 4 is an example of an image formed with only two pixels. However, a typical embodiment may use a large number of pixels to form an image. Infrared sensors 120A and 120B are arranged to receive infrared radiation 104A, B which passes through an optional infrared lens, filter, or other element 130A, B, respectively. In the configuration shown in FIG. 4, sensors 120A and 120B are formed using infrared sensitive transistors 132A and 132B, respectively, which couple to electrical ground through resistors 122A and 122B. However, the invention can be implemented using any type of thermal sensor including thermopiles, photo diodes or others. Transistors 132A and 132B are coupled to a positive power supply voltage and provide an output to processing circuitry 102 shown in FIG. 3 upon receipt of sufficient infrared radiation 104A,B to turn transistors 132A,132B "on." Although FIG. 4 illustrates the infrared sensor as implemented using a transistor, any appropriate type of infrared sensing technology may be employed. Examples include infrared sensitive diodes, charge coupled devices (CCDs), complimentary metal-oxide-semiconductor (CMOS) devices or others. In the embodiment of FIG. 4, two individual sensors are shown. However, the sensors may be formed in a one or two-dimensional array or matrix. Thus, a captured thermal image can be obtained using just two individual infrared sensors with each sensor corresponding to a subsection or region within the image, or can be formed using a larger number of individual sensors to form a larger matrix or array.

In operation, infrared sensors 120A and 120B are directed (aimed) to receive infrared radiation 104A and 104B from different locations 106A and 106B on conduit 32. The specific shape and size of locations 106A,B will be dependent upon the characteristics of sensors 120A,B, lens 130A,B and the spacing and relative orientation between the detector 100 and the process conduit 32. The outputs from sensors 120A,B are provided to processing circuitry 102. For example, processing circuitry 102 can digitize the outputs from sensors 120A,B and provide a digital signal to microprocessor 24.

Figure 5:
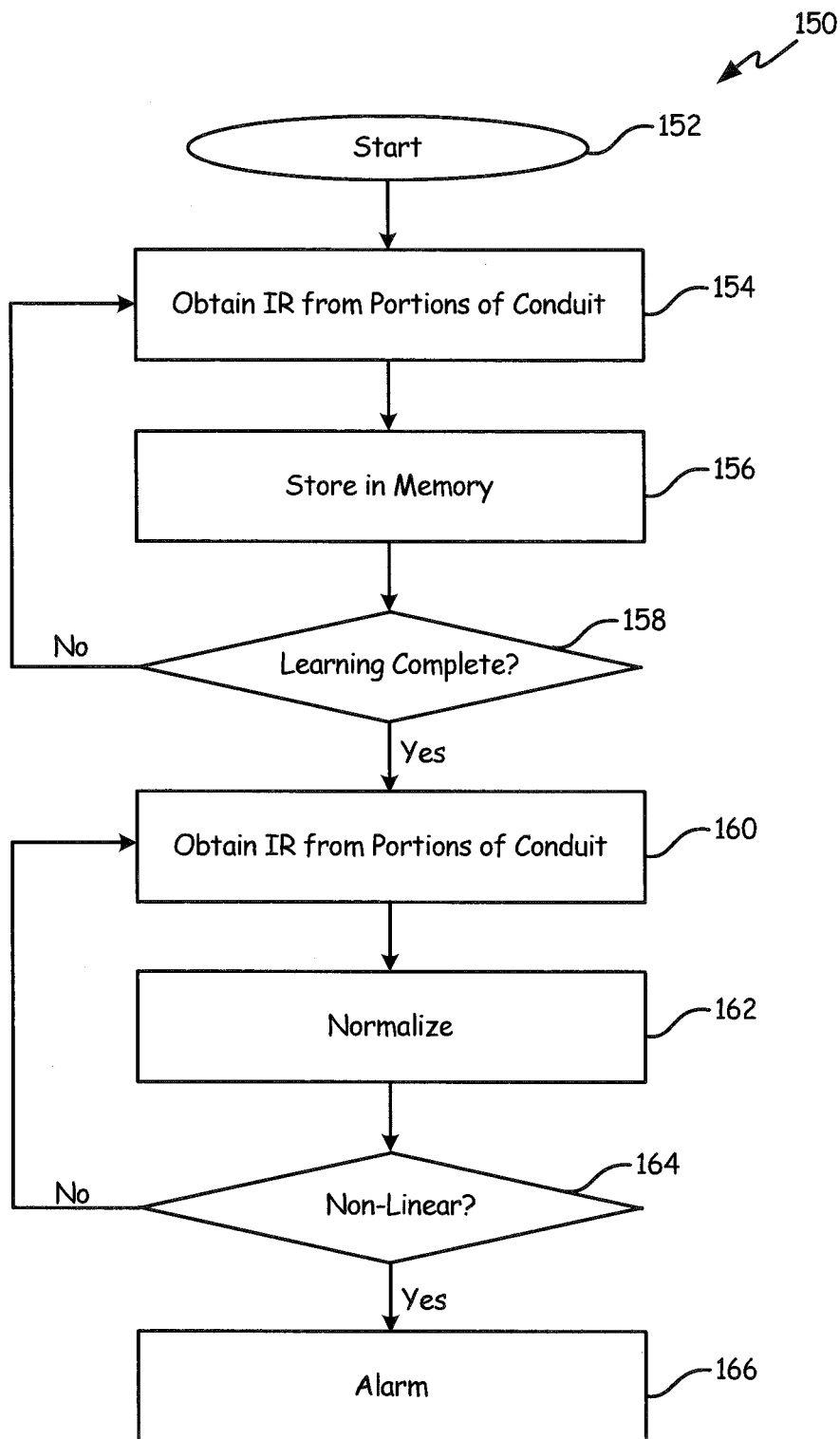
FIG. 5 is a simplified block diagram showing example step for detecting a process anomaly.

FIG. 5 is a simplified block diagram 150 showing steps performed by microprocessor 24 shown in FIG. 3 in accordance with one example embodiment. The steps shown in diagram 150 can be embodied in programming instructions stored in memory 26. The process is initiated at block 152. At block 154, infrared radiation 104 from portions of conduit 32 is collected using detector 100, digitized by processing circuitry 102 and provided to microprocessor 24. At block 156, information related to the received radiation is stored in memory 26 as thermal profile information for the process conduit 32 during normal operation of the process. This information may be in the form which identifies a portion of the conduit 32 and its normal average temperature. This is used to obtain a temperature characterization or profile of various portions 106 of the conduit 32 from which the radiation 104 originated during normal operation of the process. At block 158, control is returned to block 154 if the learning process has not completed. Blocks 154 and 156 provide a learning period or phase during which normal process operation can be observed. The learning period is terminated at block 158 as desired. For example, this may be after a certain period of time, upon receipt of a command, or based on some other occurrence. After completion of the learning period, a monitoring period or phase begins at block 160 where infrared radiation is again sensed by detector 100. At block 162, the sensed radiation is normalized. The information stored in memory 26 during the learning period is retrieved and the normal temperature value subtracted from the current temperature for each location of conduit 32 being monitored. At block 164, the normalized temperature information is analyzed to determine if it provides a linear profile or if it is non-linear due to a temperature anomaly such as is illustrated in FIG. 2B. This profile is typically formed based upon the normalized temperature values for adjacent locations along conduit 32. In order to determine if the profile is linear, the temperature of at least three locations along conduit 32 must be monitored. Further, the sensitivity can be adjusted by providing an absolute or relative amount from which the temperature profile may deviate from a straight line. If the profile is linear, control is returned to block 160 and the monitoring period continues. If a non-linearity is detected, control is passed to block 166 and an alarm is provided. This can be output, for example, on process control loop 18 using I/O circuitry 30 shown in FIG. 3 and may include information related to the location of the detected anomaly and the intensity of the anomaly.

FIG. 6 is a simplified block diagram of another example implementation of infrared detector 100. In the embodiment of FIG. 6, infrared detector 100 is formed by an array of infrared sensors 120-1 . . . 120-N. This array may, for example, be a one-dimensional linear array. In another configuration, detector 100 is a two-dimensional array or matrix, for example, as found in a thermal imaging system. One example thermal imaging system is the Optrix PI-160 thermal imaging camera. FIG. 6 illustrates 4 portions or slices 106A, 106B, 106C and 106D having respective thermal radiation outputs 104A-D. Infrared radiation 104A-D are directed to different locations on sensor 100 whereby different sensors 120 are activated. Processing circuitry 102 receives information related to the intensity of the thermal radiation received by each of the sensors 120. This information is provided to the microprocessor 24 through processing circuitry 102 which comprises an analog to digital converter. Based upon this information, the microprocessor 24 can identify a location of a process anomaly as discussed above.

The infrared detector 100 and/or processing circuitry 102 may be located remotely from the device 12 and communicate over a data connection. The data connection may be any appropriate type of connection including wired techniques, for example, a USB connection, as well as wireless communication techniques including WirelessHART®, BlueTooth®, etc. Further, the infrared detector 100 and/or processing circuitry 102 may be affixed to the housing of device 12 or formed integrally with the housing of device 12. In one configuration, the direction of the infrared detector 100 can be adjusted by an operator during installation to point at a desired location. In another example embodiment, pan and/or tilt actuators are provided allowing the infrared detector 100 to be moved during operation. In one configuration, a hand-held device or the like is used during installation whereby a thermal output from the detector 100 may be observed by the installation personnel to ensure that the infrared detector 100 is pointed as desired.

Although the present invention has been described with reference to preferred embodiments, workers skilled in the art will recognize that changes may be made in form and detail without departing from the spirit and scope of the invention. A process anomaly can be detected as discussed above. A simple comparison and a threshold may be used, or more complex configurations including, for example, neural networks or other logic may be implemented. Additionally, the process anomaly detection can be based upon some additional input such as a process variable. The detection can further be a function of the current time, sensed process variables, the particular state a process is in, the ambient temperature, etc. Trends in the normalized temperature profile may also be observed and used for anomaly detection. The diagnostic circuitry described herein can be implemented in hardware or software and includes both analog and digital implementations. For example, one or both of the processing circuitry 102 and the microprocessor 24 may implement the diagnostic circuitry. In another example embodiment, the thermal image information is transmitted to another location at which the diagnostic circuitry resides. The thermal profile information can also be loaded during manufacture or loaded during commissioning of the device. The profile does not need to be learned as discussed above and can be selected from a number of standardized profiles or based upon modeling information. If a hot or cold anomaly is detected, the device 12 can be used to predict an impending failure thereby allowing maintenance to be scheduled at a desired time. An output can be provided which indicates that a conduit should be clean due to excessive build up of material within the conduit. The rate of temperature change of various areas of the conduit relative to other areas can provide an indication of a change in the process dynamics such as a change in flow rate or a build up of material. Individual spot sensors may be used in addition to array described above. The collected thermal information may be transmitted to another location such as a control room for more detailed evaluation. Other techniques may be used to detect a process anomaly. As used herein, the term "determining" includes detecting and/or diagnosing. In addition to a diagnostic output, a temperature output can also be provided which is representative of the temperature of the process conduit based upon the received infrared radiation. Note that the process of identifying a non-linear relationship between a plurality of pixel outputs includes storing information in a memory. In this context, the stored information used to identify non-linear relationship is "thermal profile information". The thermal profile information stored in the memory may be information related to normal temperature levels, may be dynamic information which changes during process operation or may be of some other type. Typically, the process device 12 is a stationary field device mounted at a fixed location. The device can be configured to continuously monitor a process conduit.

What is claimed is:

1. A diagnostic field device for detecting a condition of a process conduit which carries a process fluid in an industrial process, comprising:
an infrared detector comprising a plurality of pixels configured to receive infrared radiation from the process conduit and responsively provide a plurality of pixel outputs, wherein a first pixel of the plurality of pixels is configured to receive infrared radiation from a first location on the process conduit, a second pixel of the plurality of pixels is configured to receive infrared radiation from a second location on the process conduit and a third pixel configured to receive infrared radiation from a third location on the process conduit and responsively provide an output;

a memory containing thermal profile information related to outputs from the first, second and third pixels during normal operation of the industrial process;

a microprocessor configured to normalize the outputs from the first, second and third pixels using the thermal profile information contained in the memory and further configured to identify a process anomaly related to the condition of the process conduit based upon a nonlinear relationship between normalized outputs from the first, second and third pixels; and output circuitry configured to provide a diagnostic output indicative of the identified process anomaly.

2. The diagnostic field device of claim 1 wherein the infrared detector comprises an array of pixels.

3. The diagnostic field device of claim 2 wherein an image of the first location is obtained using a first plurality of pixels and an image of the second location is obtained using a second plurality of pixels.

4. The diagnostic field device of claim 3 wherein the anomaly detection is based upon a first average of outputs from the first plurality of pixels and a second average of outputs from the second plurality of pixels.

5. The diagnostic field device of claim 4 including a third plurality of pixels arranged to obtain an image of a third location on the conduit and wherein the anomaly detection is further a function of an average of outputs from the third plurality of pixels.

6. The diagnostic field device of claim 5 wherein the first, second and third plurality of pixels are arranged to obtain images slices of the conduit.

7. The diagnostic field device of claim 1 wherein the diagnostic output includes information related to an impending failure of the conduit.

8. The diagnostic field device of claim 1 wherein the diagnostic output includes information indicating that the process conduit needs maintenance.

9. The diagnostic field device of claim 1 wherein the process anomaly is detected based upon relative rate of change between outputs from the first and second pixels.

10. The diagnostic field device of claim 9 wherein the diagnostic output includes information indicating a change in flow rate of process fluid has occurred.

11. The diagnostic field device of claim 9 wherein the diagnostic output includes information indicating a build up of material in the conduit has occurred.

12. The diagnostic field device of claim 9 wherein the conduit comprises process piping.

13. The diagnostic field device of claim 9 wherein the diagnostic output is provided on a process control loop.

14. The diagnostic field device of claim 1 wherein the output circuitry further provides an output indicative of temperature of the conduit based upon the received infrared radiation.

15. The diagnostic field device of claim 1 wherein the output circuitry provides an output on a process control loop.

16. The diagnostic field device of claim 15 wherein the process control loop comprises a wireless process control loop.

17. The diagnostic field device of claim 1 including a mount to mount the diagnostic field device at a fixed location.

18. The diagnostic field device of claim 1 wherein the diagnostic field device is configured to continuously monitor the process conduit.

19. A method of detecting a condition of a process conduit which carries a process fluid in an industrial process using a diagnostic field device, comprising:

receiving infrared radiation with an infrared radiation detector having a plurality of pixels configured to receive the infrared radiation from the process conduit and responsively provide a plurality of pixel outputs, wherein a first pixel of the plurality of pixels is configured to receive infrared radiation from a first location on the process conduit, a second pixel of the plurality of pixels as configured to receive infrared radiation from a second location on the process conduit and a third pixel configured to receive infrared radiation from a third location on the process conduit and responsively provide an output;

retrieving thermal profile information from a memory which is related to outputs from the first, second and third pixels during normal operation of the industrial process;

normalizing the outputs from the first, second and third pixels using the thermal profile information retrieved from the memory;

identifying an anomaly related to the condition of the process conduit based upon a nonlinear relationship between normalized outputs from the first, second and third pixels; and providing a diagnostic output indicative of the process anomaly.

* * * * *